United States Patent [19]

Neenan et al.

[11] Patent Number: 4,987,209
[45] Date of Patent: Jan. 22, 1991

[54] DIETHYNYL MONOMERS AND POLYMERS THEREOF

[75] Inventors: Thomas X. Neenan, Arlington; George M. Whitesides, Newton, both of Mass.

[73] Assignee: The President and Fellows of Harvard, Cambridge, Mass.

[21] Appl. No.: 281,911

[22] Filed: Dec. 7, 1988

Related U.S. Application Data

[62] Division of Ser. No. 101,632, Sep. 28, 1987, abandoned.

[51] Int. Cl.$^5$ .............................................. C08F 12/30
[52] U.S. Cl. ................................... 526/243; 526/247; 526/251
[58] Field of Search ............... 526/285, 243, 247, 251

[56] References Cited

U.S. PATENT DOCUMENTS

| | | | |
|---|---|---|---|
| 2,436,213 | 2/1948 | Hill, Jr. ................................ | 526/285 |
| 3,542,888 | 11/1970 | Ghislain et al. ..................... | 526/285 |
| 3,684,786 | 8/1972 | Chandrasekaran ................. | 526/285 |
| 3,714,276 | 1/1973 | Pierce . | |
| 4,097,460 | 6/1978 | Jabloner . | |
| 4,241,223 | 12/1980 | Baucom ............................. | 526/285 |
| 4,301,313 | 11/1981 | Marshall . | |
| 4,695,655 | 9/1987 | Lau et al. ........................... | 526/285 |

FOREIGN PATENT DOCUMENTS

| | | | |
|---|---|---|---|
| 0299384 | 1/1989 | European Pat. Off. ............ | 526/285 |
| 59-53510 | 3/1984 | Japan .................................. | 526/285 |
| 59-89310 | 5/1984 | Japan .................................. | 526/285 |
| 62-260804 | 11/1987 | Japan .................................. | 526/285 |

OTHER PUBLICATIONS

J. Chem. Soc., Aromatic Polyfluoro-compounds, Coe, et al., pp. 2626-2628 (1967).
J. Organometallic Chem., Waugh, et al., pp. 275-278 (1972).
M. Ballester, et al., Synthesis of the First Perchloroaryl--acetylenes, pp. 2353-2354 (1977).

Primary Examiner—Joseph L. Schofer
Assistant Examiner—N. Sarofim
Attorney, Agent, or Firm—Fish & Richardson

[57] ABSTRACT

The compound 1,3-diethynyl tetrafluorobenzene, and compounds having the structure

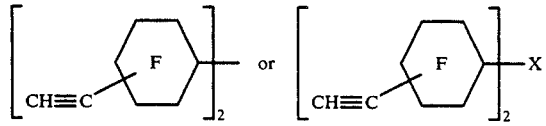

in which

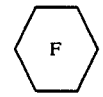

represents a perfluorinated benzene ring and X represents oxygen or sulfur, as well as homopolymers and copolymers thereof.

2 Claims, No Drawings

DIETHYNYL MONOMERS AND POLYMERS THEREOF

This invention described herein was made with Government support and the U.S. Government has certain riqhts in the invention.

This is a divisional of co-pending application Ser. No. 101,632 filed on Sept. 28, 1987 now abandoned.

This invention relates to novel diethynyl perfluorinated aromatic monomers and to polymers and copolymers thereof.

It has hitherto been proposed in Jabloner U.S. Pat. No. 4,097,460 to make certain aryl acetylenes and polymers thereof, and in Pierce et al., U.S. Pat. No. 3,714,276, there has been described 1,3 divinyl tetrafluorobenzene. It has also been proposed in Waugh et al., J. Organometallic Chem., Vol. 39, 275–278 (1972) to make 1,4-diethynyl tetrafluorobenzene and certain other ethynyl substituted perfluorinated aromatic compounds, but there was no indication that such compounds could be polymerized.

It has now been found that 1,3-diethynyl tetrafluorobenzene can be synthesized and can be polymerized and copolymerized to form cross-linked polymers and copolymers having unique properties. It has also been found that compounds having the structure

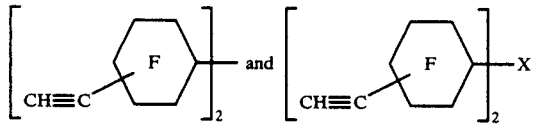

in which

represents a perfluorinated benzene ring and X represents oxygen or sulfur, (that is, bis(ethynyl tetrafluorophenyl), as well as bis(ethynyl tetrafluorophenyl) there and thioether) are monomers useful for making cross linked polymers having analoqous properties.

The monomers of the present invention are useful in making polymers and copolymers which are characterized in general by being cross-linked, resistant to oxidation and pyrolysis at elevated temperatures, soluble in organic solvents such as dioxane, 1,2-dichlorobenzene, and the like, having good tribological characteristics (surface slipperiness) and low dielectric constant as well as high hardness, and capable of being readily molded at elevated temperature and pressure. The polymers may be homopolymers and they may, if desired, be end capped or copolymerized with monoetheynyl tetrafluorobenzene or other monoetheynyl perfluorinated aromatic monomer provided the amount of the selected 1,3-diethynyl tetrafluorobenzene monomer or of the selected bis(etheynyl tetrafluorophenyl) or bis(etheynyl tetrafluorophenyl) there or thioether monomer is at least 50% by weight of the total acetylenic monomer present in the polymerization mixture. Copolymers of the monomers with each other or with other mono- or di-etheynyl or -vinyl compounds can also be made, preferably containing 50% by weight or more of the selected monomer. The polymers are useful in packaging or sealing such products as electronic chips, biomedical materials, and as general purpose synthetic resins.

1,3-dietheynyl tetrafluorobenzene can be prepared from 1,3-diiodo- or 1,3-dibromo tetrafluorobenzene by reaction with trimetheylsilyl acetylene in the presence of palladium and copper complex catalysts, then converting the resulting trimetheylsilyl-substituted etheynyl derivatives to etheynyl derivatives by alkaline ester interchange with methyl alcohol. The monomers containing two aromatic rings can be prepared by first converting the appropriate dibromo or diiodo tetrafluorobenzene or a mixture thereof to the corresponding substituted biphenyl or bis(substituted phenyl) there or thioether by conventional methods, then treating the product as described above for the preparation of the 1,3-dietheynyl tetrafluorobenzene, or by using hydroxyperopyl substituted actylene (2-methyl-3-butyn-2-ol) in place of trimethyl silyl substituted actylene.

The monomers can be polymerized in solution, for example in dioxane, in the presence of oxygen and a copper complex catalyst at temperatures from approximately 50° to approximately 100° C. The monoetheynyl perfluorinated benzene employed for end capping the polymer can be mixed with the difunctional monomer at the beginning of the polymerization reaction provided the amount of the monofunctional monomer is less than 50% by weight of the total monomer. The monomers can also be polymerized in a cyclotrimerization polymerization in solution in the presence of a Ziegler-Natta catalyst such as dietheyl aluminum chloride and titanium tetrachloride at a temperature in he approximate range −20° to 40° C.

The following specific examples are intended to illustrate more fully the nature of the invention without acting as a limitation upon its scope.

In the procedures described, all reactions for the preparation of etheynyl monomers were carried out under an atmosphere of argon in order to avoid premature polymerization.

Melting points were determined on a Thomas Hoover melting point apparatus and are uncorrected. Infrared spectra were recorded as KBr discs or as thin films on NaCl plates. $^1$H NMR spectra were recorded at 80 MHz or 300 MHz. Mass spectra were recorded at 70 eV or by GC/MS using a HP 5990A. Diisoperopylamine was distilled from KOH before use. Dietheyl ether and tetrahydrofuran (THF) were distilled from disodium benzophenone dianion before use.

EXAMPLE 1

Synthesis of 1,3-diiodotetrafluorobenzene

To a cooled solution of conc. $H_2SO_4$ (50 mL) was added in portions periodic acid (7.5 g, 33 mmol). To this clear solution was added in portions finely ground KI (16.43 g, 100 mmol), whereupon an exothermic reaction took place with the evolution of iodine vapor and the formation of a dark solution. 1,2,3,5-Tetrafluorobenzene (5 g, 33 mmol) was added dropwise and the reaction mixture was hated to 70° C. for 4 hours. Upon cooling, the solution was poured carefully onto crushed ice (200 g) and filtered to remove excess iodine. The filtrate consisted of an orange aqueous layer and a heavy dark oil. Dietheyl there (200 mL) was added to dissolve the oil and the organic layer was separated, and washed with 10% sodium thiosulfate solution, followed by washing with water and drying. The solvent was removed to yield an orange oil which was further purified by passing it through a short column of silica gel, using n-hexane as the eluting solvent. Removal of the solvent yielded 1,3-diiodotetrafluorobenzene (7.1 g) as a colorless liquid in 61% yield (based on 85% pure starting material 1,2,3,5 tetrafluorobenzene); bp 140° C. (13 torr). Mass spectrum (EI) m/z (relative intensity) 402 (M+, 37), 275 (72), 254 (5.4), 148 (100), 129 (9.3), 27 (54.8), 110 (6.0). Anal. calcd for $C_6F_4I_2$: C, 17.91; I, 63.18. Found: C, 17.52; I, 63.18.

Synthesis of 1,3-bis((-trimethylsilyl)etheynyl)tetrafluorobenzene

To a solution of 1,3 diiodotetrafluoroenzene (2) (52.0 g, 130 mmol) in freshly distilled diisoperopylamine (600 mL) was added dichlorobis(benzonitrile) palladium (1.68 g, 2.4 mmol), triphenylphosphine (1.26 g, 4.8 mmol) and copper (II) acetate hydrate (0.47 q, 2.4 mmol). The solution was degassed by passing a rapid stream of argon thorough it. (Trimtheylsilyl) acetylene (TMSA) (28 g, 2.2 equiv) was added over 1 h at room temperature to the clear yellow-green solution. The solution changed color rapidly to a yellow brown with the formation of a heavy precipitate. The solution was heated at reflux until GC analysis indicated that all starting material had disappeared, approximately 6 hours. The solution was allowed to cool to room temperature and was filtered to remove the precipitate of disopropyl ammonium bromide hydrobromide salts. The solvent was removed at reduced pressure and the residue was taken up in methylene chloride. Extraction with 5% HCl followed by extraction with water (twice), drying of the organic layer and removal of the solvent yielded the crude product as a dark oil. The oil was taken up in the minimum amount of hexanes (20 mL) and applied to a silica gel column (200 g) packed in hexanes. Elution with hexanes removed first 1,4-bis(-trimethylsily)butadiene (0.65 g) followed by the desired 1,3-bis((trimethylsilyl)ethynyl)tetrafluorobenzene as colorless crystals in 92% yield; mp 55°−57° C. IR (KBr), 2980, 2920, 2080, 1505, 1260, 990, 850 cm $^{-1}$. $^1$H NMR (80 MHz, $CDCl_3$0.28 (s); Mass spectrum (EI) m/z (rel. intensity) 342 M+, 22.4), 327 (100), 156 (10.7); Anal. Calcd for $C_{16}H_{18}F_4Si_2$: C, 56.14; H, 5.26. Found: C, 56.34; H, 5.34.

1,3Diethynyltetrafluorobenzene

To a solution of 1,3-bis((trimethylsily)ethynyl)-benzene (34.2 g, 100 mmol) in degassed methanol (400 mL) was added KOH (28 mg, 05. mmol) in 1 mL of water. The solution was stirred at room temperature for 20 min. when analysis indicated that the reaction was complete. The reaction mixture was diluted with water (500 mL) and extracted with n-pentane until the extracting solvent was free of product. The combined organic layers were dried over magnesium sulfate and the solvent removed at reduced pressure at room temperature. The residue was distilled at 55° C. and 1.0 torr to yield 1,3-diethynyltetrafluorobenzene (18.0 g, 91%) as a color less liquid. IR (Film on NaCL) 3300, 2130, 1480 cm$^{-1}$. $^1$H NMR (80 MHz, $CDCl_3$) 3.50 (s, 2 H); Anal. Calcd. for $C_{10}H_2F_4C$, 60.60: H, 1.01. Found: C, 60.68; H, 0.94.

EXAMPLE 2

Synthesis of Poly(1,3-diethynyltetrafluorobenzene)

A 4 necked 3000 mL round bottomed flask fitted with a reflux condenser, a gas inlet tube, a thermometer and an addition funnel was charged with a mixture of p-dioxane (1000 mL) and pyridine (100 mL). To this mixture was added CuCl (0.78 g, 8 mmol) and 1.16 g, 10 mmol) N, N', tetramethylethylene diamine (TMEDA). Oxygen was bubbled through the solution while the temperature are gradually raised to 60°-65° C. To the deep blue-green solution was added a mixture of 1,3-diethynyl-tetrafluorobenzene (40 g, 200 mmol) and, as an end capping or copolymerizing monofunctional monomer, monoethynylpentafluorobenzene (15.36 g, 80 mmol) in p-dioxane (200 mL). The temperature rose to 75° C. Heating was continued at this temperature for 2 hours and the reaction mixture was then allowed to cool to room temperature. Oxygen addition was continued for a further 4 hours, whereupon a white precipitate gradually separated from solution. The solvent volume was reduced to half by means of a rotary evaporator and the residual mixture was poured into a rapidly stirred mixture of methanol (1500 mL) containing 15 mL of concentrated hydrochloric acid. The crude product precipitated as a heavy off-white powder which was recovered by filtration. The product was thoroughly washed with water (1000 mL), followed by washing with methanol (500 mL), and was further purified by dissolving in toluene (800 mL) and drying the solution by means of the addition of magnesium sulfate. The solution was filtered and the filtrate was treated with ethylene diamine (5 mL), then heated to 70° C. under nitrogen and maintained at this temperature for twenty minutes. The solution was hot filtered to remove a deep blue precipitate of copper salts, then was cooled and extracted with 5% HCl (3×200 mL) followed by extraction with distilled water (3×200 mL). The polymer solution was concentrated to 300 mL under reduced pressure and the product recovered as before by pouring the mixture into methanol (1000 mL) to precipitate the polymer. The product was collected by filtration and washed successively with diethyl ether (200 mL) and n-pentane (200 mL). the final product was a off-white non-melting powder. A total of 38.6 g (69.6%) of product was recovered. IR (NaCl) 2220 (w), 1620 (s), 1520 (s), 1480 (vs), 1400 (s), 1120 (s), 990 (m) 965 (vs), 910 (m). $^{19}$F NMR ($p$-dioxane-$d_8$) 220.4, 202.4, 190.8, 176.1, 164.4, 163.9. Calcd. for DP=5, C, 58.14, H, 0.00, F, 41.85. Found: c, 58.23: H, 0.33; F, 37.14. The product was capable of being molded at temperatures from 40° to 150° C. at moderate (up to 10,000 psi) pressures. In contrast, the polymer of 1,4-diethynyl tetrafluorobenzene made under the same conditions was rigid and brittle and incapable of being molded under such conditions. In addition, the polymer of the 1,3-difunctional monomer was soluble in dioxane and in 1,2-dichlorobenzene, whereas the 1,4-difunctional polymer was essentially insoluble in such solvents.

EXAMPLE 3

Bis(4,4'-dibromo-tetrafluorophenyl)sulfide

A solution was prepared of 1,4-dibromotetra fluorobenzene (20 g, 65 mmol) in a mixture of n-hexane and dietheyl ether (3:2 v/v) (500 mL). The solution was cooled to −78° C. and to this solution was added n-butyellithium (1 equiv, 40 mL of a 1.6M solution) dropwise over 30 min. The resulting yellow solution was stirred at −78° C. for 3 h. To this solution was added sulfur dichloride (SCl$_2$) (0.5 equiv, 3.35 g, 33 mmol) dropwise in one portion over 5 min. The solution was stirred at −78° C. for a further 1.5 hours and then allowed to warm to room temperature. Water (10 mL) was added and the solution was allowed to stand overnight. The yellow solution was extracted with water (3×300 mL) and dried (MgSO$_4$). The solvent was removed to yield an oily yellow solid, which was dissolved in n-hexane and passed through a short column of silica; the solvent was removed to yield the product as white cubic crystals. A total of 10 g (62%) of the desired product was recovered. The melting point was 105°–107° C. IR (KBr) 1450, 1240, 940, 790; Mass Spectrum (EI), (Rel. intensity) 490 (53.8), 488 (100), 486 (50.7), 409 (12.3), 407 (11.3), 328 (23.1). Anal. Calcd. for C$_{12}$Br$_2$F$_8$S: C, 29.63, F, 31.27. Found: C 29.61; F 30.70.

Synthesis of (4,4'-bis(3 hydroxy-3 methyl 1-butynyl) tetrafluorophenyl) sulfide

To a solution of bis(4,4'-dibromo tetrafluoro phenyl) sulfide (4.86 g, 10 mmol) in dry deoxygenated diisopropylamine was added dichlorobis(triphenylphosphine) palladium (700 mg, 1 mmol) and copper (1) acetate (200 mg, 1 mmol). The solution was cooled by means of an ice bath and to the cooled solution was added 2-methyl-3-butyn-2ol-(2.13 g, 25 mmol). The solution was allowed to warm to room temperature over a period of 1 hour and was then heated at reflux for a period of 24 hours. The solution was cooled and filtered to remove the precipitate of diisopropylammonium bromide. The residue was dissolved in methylene chloride, extracted with water, the organic layer was dried (magnesium sulfate), and the solvent removed. The residue was chromatographed on silica gel using diethyl ether/hexane (3:7 v/v) as the eluent. A white crystalline compound was removed from the column which was identified by mass specterometry as 1,4 bis-(3 hydroxy 3-methyl-1-butynyl)tetrafluorobenzene. Further elution with dietheyl ether/hexane (1:1 v/v) then yielded the desired product as pale yellow crystals. The yield was 2.2 g (44.5%), mp 148-150 C. IR (KBr) 3300, 2980, 2220, 1360, 1190, 1150, 975, 940 cm$^{-1}$. $^1$H NMR (80 MHz, d$_6$-acetone) δ2.8(s, 2H), 1.55(s, 12H); Mass Spectrum (EI)(rel. intensity) 494 (1.0), 479 (0.3), 262 (100). Anal. Calcd. or C$_{22}$H$_{14}$F$_8$O$_2$S: C, 53.44; H, 2.83. Found: C, 53.87, H 2.62.

Synthesis of (4,4'-diethynyloctafluorophenyl) sulfide

This compound was prepared by the basic hydrolysis of (bis-4,4'(3-hydroxy 3-methyl 1-butynyl)octafluorophenyl) sulfide using a procedure analogous to the preparation of 1,4'dietheynyloctafluorobiphenyl described above. From 4 g of starting material there was obtained 2.23 g (73%) of product as tan colored crystals. IR(KBr) 3320, 2110, 1480, 1190, 1160, 980, 960 cm$^{-1}$. $^1$H NMR (CDCl$_3$) δ3.82(s). Mass Spectrum (E) (rel. intensity) 378 (2.0), 354 (100) Anal. Calcd or C$_{16}$H$_2$F$_8$S: C, 50.79; H, 0.71. Found: C, 51.03; H, 0.82.

EXAMPLE 4

Synthesis of poly(bis(4,4'-dietheynyltetrafluoro phenyl) sulfide)

A 4 necked 1000 mL round bottomed flask fitted with a reflux condenser, a gas inlet tube, a thermometer and an addition funnel was charged with a mixture of p-dioxane (500 mL) and pyridine (20 mL). To this mixture was added CuCl (0.20 q, 2 mmol) and 0.29 g, 2.5 mmol) of TMEDA. Oxygen was bubbled through the solution while the temperature was gradually raised to 60°–65° C. To the deep blue-green solution was added a mixture of bis(4,4'-dietheynyltetrafluorophenyl) sulfide (3.78 g, 10 mmol) and monoetheynylpentafluorobenzene (0.96 g, 5 mmol) in p-dioxane (30 mL). The temperature rose to 70° C. Heating was continued for 2 hours and the reaction mixture was allowed to cool to room temperature. Oxygen addition was continued for a further 3 hours. The solvent volume was reduced to one third by means of a rotary evaporator and the residual mixture was poured into a mixture of rapidly stirring methanol (200 mL) containing 2 mL of concentrated hydrochloric acid. The crude product precipitated as a heavy off-white powder which was recovered by filtration. The product was thoroughly washed with water (500 mL), followed by washing with methanol (300 mL). The polymer was dissolved in toluene (200 mL) and the solution was dried by means of the addition of magnesium sulfate. The solution was filtered and the filtrate was treated with ethylene diamine (2 mL), then heated to 70° C. under nitrogen and maintained at this temperature for fifteen minutes. The solution was hot filtered to remove a small amount of pecipitated copper salts, cooled, and extracted with 5% HCl (two 200 mL portions) followed by extraction with distilled water (there 200 mL portions). The polymer solution was concentrated to 100 mL under reduced pressure and the product recovered as before by precipitation of the mixture into methanol (400 mL). The product was collected by filtration and washed successively with dietheyl ether (200 mL) and n-penane (200 mL). A total of 3.5 g (73.8%) of product was recovered. IR (NaCl) 2230 (m), 1625 (s), 1530 (s), 1470 (s), 1220 (s), 990 (m), 940 (vs) cm$^{-1}$. Anal. Calcd. for C$_{32}$F$_{18}$S, C, 50.66, H, 0.00, F, 45.11. Found: C, 51.23; H, 0.39; F, 44.32.

EXAMPLE 5

Synthesis of 4,4'-bis(3-hydroxy-3-methyl-1-butynyl)octafluorobiphenyl

To a solution of 4,4'-dibromooctafluorobiphenyl (10 g, 21.9 mmol) in degassed diisopropylamine (350 mL) was added dichlorobis(triphenylphosphine) palladium (770 mg, 1.05 mmol, 5 mol %) and copper (1) acetate (219 mg, 1.05 mmol, 5 mol %). The solution was cooled to 0° C. and to this solution was added 2-methyl 3 butyn 2-ol (2.2 equivalents, 4.0 g, 4.7 mL). The solution was allowed to warm to room temperature and was subsequently heated at 50° C. for 12 hours. The solution was cooled and filtered to remove the pecipitate of diisopropylammonium bromide. The solvent was removed at reduced pressure and the residue was chromatographed on a column of silica gel (200 g) packed with ethel acetate. An oily yellow solid was removed from the column. The addition of a couple of drops of methanol caused the oil to solidify. The resulting solid was recrystallized from a mixture of ethyl acetate/hexane (1:2) to yield 4,4'-bis(3 hydroxy-3-methyl 1-butynyl)-octafluorobiphenyl as white crytals. The yield was 8.6 (92%), mp 119°–121° C. IR (KBr) 3400, 2960, 1475, 1365, 1210, 1170, 990, 962 cm$^{-1}$. $^1$H NMR (80 MHz, CDCl$_3$) δ2.7 (s, 2H), 1.53 (s, 12H); Mass Spectrum (EI)(rel. intensity 462 (3.7), 447 (44.0), 432 (1.5); Anal. Calcd for C$_{22}$H$_{14}$F$_8$O$_2$: C, 57.14; H, 3.03. Found: C,60.60; H, 4.78

Synthesis of 4,4'-dietheynyloctafluorobiphenyl

A solution of the compound described above (7.0 g, 15.1 mmol) was prepared in freshly distilled toluene. The resulting solution was deoxygenaed with dry nitrogen and to this solution was added powdered KOH (1.0 g, 16.6 mmol). The solution was heated at reflux for 1 hour and the evolution of acetone was monitored by GC. The resulting dark solution was cooled to room temperature and the toluene was removed. The dark residue was dissolved in the minimum amount of metheylene chloride and passed through a short column of silica. The solvent was removed from the pale yellow eluent to yield 4,4'-dietheynyloctafluorobiphenyl as a off-white solid. The yield was 4.6 g, (84.0%). IR (KBr) 3300, 2100, 1620, 1465, 1385, 1270, 990, 719, 670 cm$^{-1}$. $_1$H (80 MHz, CDCl$_3$) 3.75 (s); Mass Spectrum (EI)(rel. intensity) 322 (100), 253 (27.6); Anal. Calcd. for C$_{16}$H$_2$F$_8$: C, 55.49; H, 0.57. Found: C,55.32; H, 0.95

EXAMPLE 6

Synthesis of Poly(4,4'-dietheynyloctafluorobiphenyl)

A 4-necked 1000 mL round bottomed flask fitted with a reflux condenser, a gas inlet tube, a thermometer and an addition funnel was charged with a mixture of p-dioxane (500 mL) and pyridine (20 mL). To this mixture was added CuCl (0.39 g, 4 mmol) and TMEDA (0.58 q, 5 mmol). Oxygen was bubbled through the solution while the temperature was gradually raised to 60°–65° C. To the deep blue-green solution was added a mixture of 4,4'-dietheynyloctafluorobiphenyl (5.9 g, 17 mmol) and monoethynylpentafluorobenzene (1.56 g, 8 mmol) in p-dioxane (50 mL). The temperature rose to 75° C. Heating was continued for 2 hours and the reaction mixture was allowed to cool to room temperature. Oxygen addition was continued for a further 4 hours. A white precipitate gradually separated from solution. The solvent volume was reduced to one third by means of a rotary evaporator and the residual mixture was poured into a mixture of rapidly stirring methanol (600 mL) containing 5 mL of concentrated hydrochloric acid. The crude product precipitated as a heavy off-white powder which was recovered by filtration. The product was thoroughly washed with water (1000 mL), followed by washing with methanol (500 mL). The polymer was dissolved in toluene (300 mL) and the solution dried by means of the addition of magnesium sulfate. The solution was filtered and the filtrate was treated with ethylene diamine (5 mL). The solution was heated to 70° C. under nitrogen and maintained at this temperature for twenty minutes, after which it was hot filtered to remove a deep blue precipitate of copper salts. The solution was then cooled and extracted with 5% HCl (there 200 mL portions) followed by extraction with distilled water (there 200 mL portions). The polymer solution was concentrated to 100 mL under reduced pressure and the product recovered as before by precipitation of the mixture into methanol (1000 mL) and filtration, and washed successively with diethyl ether (200 mL) and n pentane (200 mL). A total of 6.2 g (82.6%) of product was recovered. IR (NaCl) 2220 (w), 1620 (s), 1530 (s), 1470 (vs), 1380 (s), 1220 (s), 990 (m), 960 (vs), cm$^{-1}$. Anal. Calcd for C$_{32}$F$_{18}$, 18, 52.89, F, 47.10. Found: C, 51.98; F, 46 66.

What is claimed is:

1. Homopolymers and copolymers of a compound having the structure

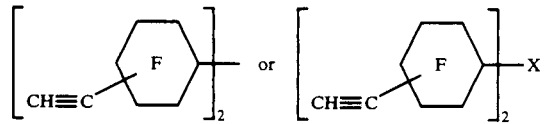

in which

represents a perfluorinated benzene ring and X represents oxygen or sulfur in which said compound amounts to at least 50% by weight of said polymers.

2. Homopolymers and copolymers of 1,3-diethynyl tetrafluorobenzene containing at least 50% by weight of said 1,3-diethynyl tetrafluorobenzene.

* * * * *

UNITED STATES PATENT AND TRADEMARK OFFICE
CERTIFICATE OF CORRECTION

Page 1 of 3

PATENT NO.  : 4,987,209

DATED       : January 22, 1991

INVENTOR(S) : Thomas X. Neenan and George M. Whitesides

It is certified that error appears in the above-identified patent and that said Letters Patent are hereby corrected as shown below:

On the Title Page:
In <u>Other Publications</u>:

Insert --Tetrahedron Letters-- before "Synthesis".

In the <u>Specification</u>:

Col. 1, line 45, "there" should be --ether--;
      line 46, "analoqous" should be --analogous--;
      line 57, "monoetheynyl" should be --monoethynyl--;
      line 58, "monoetheynyl" should be --monoethynyl--;
      line 61, each occurrence of "etheynyl" should be --ethynyl--;
      line 62, "there" should be --ether--;

Col. 2, lines 4,8,9,17,23,39; "etheynyl" should be --ethynyl--;
      line 6, "trimetheylsilyl" should be --trimethylsilyl--;
      line 8, "trimetheylsilyl" should be --trimethylsilyl--;
      line 14, "there" should be --ether--;
      line 18, "yperopyl" should be --ypropyl--;
      line 33, "he" should be --the--;
      line 47, "Disoperopyla" should be --Diisopropyla--;
      line 62, "hated" should be --heated--;
      line 66, "there" should be --ether--;

Col. 3, line 9, "27" should be --127--;
      line 14, "etheynyl" should be --ethynyl--;
      line 17, "diisoperopylamine" should be --diisopropylamine--;
      line 32, "disopropyl" should be --diisopropyl--;
      line 32, delete "hydrobromide";
      line 46, insert --(-- before "$M^+$,";

UNITED STATES PATENT AND TRADEMARK OFFICE
CERTIFICATE OF CORRECTION

PATENT NO. : 4,987,209

DATED : January 22, 1991

INVENTOR(S) : Thomas X. Neenan and George M. Whitesides

It is certified that error appears in the above-identified patent and that said Letters Patent are hereby corrected as shown below:

Col. 3, line 54, "05. should be --0.5--;
line 65, "Film" should be --film--;

Col. 4, line 66, "dietheyl" should be --diethyl--;
line 68, "butyellithium" should be --butyllithium--;

Col. 5, line 33, "orqanic" should be --organic--;
line 40, "dietheyl" should be --diethyl--;

Col. 6, line 1, "0.20 q" should be --0.20 g--;
line 1, insert --(-- before "0.29 g";
line 2, "throuqh" should be --through--;
line 6, "monoetheynylpentafluorobenzene" should be --monoethynylpentafluorobenzene--;
line 27, "there" should be --three--;
line 32, "dietheyl" should be --diethyl--;
line 53, "pecipitate" should be --precipitate--;
line 57, "ethel" should be --ethyl--;

Col. 7, line 12, "theylene" should be --thylene--;
line 14, "dietheynyloctafluorobiphenyl" should be --diethynyloctafluorobiphenyl--;
line 19, insert --.-- after "0.95";
line 22, "dietheynyloctafluorobiphenyl" should be --diethynyloctafluorobiphynyl--;
line 28, "0.58q" should be --0.58 g--;

UNITED STATES PATENT AND TRADEMARK OFFICE
CERTIFICATE OF CORRECTION

PATENT NO. : 4,987,209

DATED : January 22, 1991

INVENTOR(S) : Thomas X. Neenan and George M. Whitesides

It is certified that error appears in the above-identified patent and that said Letters Patent are hereby corrected as shown below:

Col. 8, line 9, "there" should be --three--;
       line 10, "there" should be --three--;
       line 16, "n pentane" should be --n-pentane--.

Signed and Sealed this

Sixth Day of April, 1993

*Attest:*

STEPHEN G. KUNIN

*Attesting Officer*      *Acting Commissioner of Patents and Trademarks*